United States Patent [19]

Wahle et al.

[11] Patent Number: 5,723,137

[45] Date of Patent: Mar. 3, 1998

[54] PROCESS FOR THE PRODUCTION OF STORAGE STABLE WAX DISPERSIONS

[75] Inventors: Bernd Wahle, Kaarst; Peter Waltenberger, Breitscheid; Claudia Klink, Willich; Thomas Foerster, Erkrath; Thomas Engels, Frechen, all of Germany

[73] Assignee: Henkel Kommanditgesellschaft auf Aktien, Duesseldorf, Germany

[21] Appl. No.: 637,638

[22] PCT Filed: Oct. 20, 1994

[86] PCT No.: PCT/EP94/03453

§ 371 Date: Apr. 29, 1996

§ 102(e) Date: Apr. 29, 1996

[87] PCT Pub. No.: WO95/11936

PCT Pub. Date: May 4, 1995

[30] Foreign Application Priority Data

Oct. 29, 1993 [DE] Germany ............ 43 37 030.6

[51] Int. Cl.$^6$ ............... A61K 7/06; A61K 7/48
[52] U.S. Cl. ............... 424/401; 424/70.1; 424/63; 514/937; 514/943; 514/941; 8/115.6
[58] Field of Search ............... 424/401, 70.1, 424/63; 514/937, 943, 941; 8/115.6

[56] References Cited

U.S. PATENT DOCUMENTS

| | | | |
|---|---|---|---|
| 4,379,755 | 4/1983 | Yamada | 252/312 |
| 4,446,127 | 5/1984 | Büchler et al. | 424/59 |
| 5,028,265 | 7/1991 | Schmidt-Thuemmes et al. | 106/271 |
| 5,196,417 | 3/1993 | Dolling | 514/226.5 |

FOREIGN PATENT DOCUMENTS

| | | |
|---|---|---|
| 045008 | 2/1982 | European Pat. Off. . |
| 345586 | 12/1989 | European Pat. Off. . |
| 410262 | 1/1991 | European Pat. Off. . |
| 3819193 | 12/1989 | Germany . |
| 4010393 | 10/1991 | Germany . |
| 4140562 | 6/1993 | Germany . |

OTHER PUBLICATIONS

Encyclopedia of Emulsion Technology, vol. I, P. Becher (ed.), Marcel Decker, New York 1983, p. 337 et seq.
O.-A. Neumüller, "Römpps Chemie-Lexikon". 7th Edition, Stuttgart 1977, p. 3857.
Zeitschrift für Lebensmitteltechnologie, 1979, vol. 30(6), pp. 256–264.
"Emulgatoren für Lebensmittel", Springer-Verlag, 1985 (reference unavailable).
Römpps Chemie-Lexikon, O.-A. Neumüller (ed.) 7th Edition Stuttgart 1977, p. 3615 et seq.
Soap Cosm. Chem. Spec. 1987 (4) p. 52.
Römpps Chemie-Lexikon, 7th Edition, Stuttgart 1975, pp. 3336 et seq.

*Primary Examiner*—Thurman K. Page
*Assistant Examiner*—D. Faulkner
*Attorney, Agent, or Firm*—Ernest G. Szoke; Wayne C. Jaeschke; Real J. Grandmaison

[57] ABSTRACT

A process for producing a storage-stable, fine-particle wax dispersion by heating a mixture containing (A) 10% to 80% by weight of a wax, (B) 0.5% to 30% by weight of a hydrophilic nonionic dispersant having an HLB value of 8 to 18, and (C) 1% to 30% by weight of a hydrophobic co-dispersant selected from the group consisting of fatty alcohols containing 12 to 22 carbon atoms and partial esters of polyols containing 3 to 6 carbon atoms with fatty acids containing 12 to 22 carbon atoms, with the proviso that the weight ratio of component (B) to component (C) is in the range from 0.5:1 to 20:1, in the presence of 15% to 85% by weight of water to a temperature above the melting point of the mixture of components (A) to (C) to form a dispersion, heating the dispersion to its phase inversion temperature, and then cooling the dispersion to a temperature below its phase inversion temperature.

19 Claims, No Drawings

PROCESS FOR THE PRODUCTION OF STORAGE STABLE WAX DISPERSIONS

BACKGROUND OF THE INVENTION

1. Field of the Invention

This invention relates to a process for the production of wax dispersions under conditions which lead to fine-particle long-life dispersions.

2. Discussion of Related Art

It is known that oil-in-water emulsions (hereinafter referred to as o/w emulsions) prepared with nonionic emulsifiers and stabilized undergo phase inversion on heating. As a result of the phase inversion process, the outer aqueous phase becomes the inner phase at relatively high temperatures. This process is generally reversible, i.e. the original emulsion type is reformed on cooling. It is also known that the position of the phase inversion temperature depends on many factors, including for example the type and phase volume of the oil component, the hydrophilicity and structure of the emulsifier or the composition of the emulsifier system, cf. for example K. Shinoda and H. Kunieda in Encyclopedia of Emulsion Technology, Volume I, P. Becher (ed.), Marcel Decker, New York 1983, pages 337 et seq.

DE-A-38 19 193 describes a process for the production of low-viscosity o/w emulsions by the phase inversion technique. In this process, the phase inversion technique is applied to mixtures containing an oil component, a nonionic emulsifier and a co-emulsifier in aqueous medium. The oil component is said to consist of 50 to 100% of special mono- or diesters, 0 to 50% of $C_{8-22}$ fatty acid triglycerides and optionally 0 to 25% of a hydrocarbon.

DE-A-41 40 562 describes a process for the production of o/w emulsions containing particularly polar oils by the phase inversion technique. Particularly polar oils are understood to be oils which have a dipole moment above 1.96 D. In this process, the technique of phase inversion is applied to mixtures containing the particularly polar oils mentioned, a nonionic emulsifier, optionally a co-emulsifier and an interfacial moderator selected from the group of tocopherols, Guerbet alcohols containing 16 to 20 carbon atoms or asteroid containing 1 to 3 OH groups.

DE-A-38 19 193 and DE-A-41 40 562 do not disclose any other components beyond those mentioned. In particular, these documents do not contain any reference to whether and by what measures fine-particle long-life wax dispersions can be produced.

DESCRIPTION OF THE INVENTION

The problem addressed by the present was to provide a process for the production of fine-particle long-life wax dispersions.

According to the invention, the solution to this problem is characterized in that (A) 10 to 80% by weight of a wax are heated with (B) 0.5 to 30% by weight of a hydrophilic nonionic dispersant with an HLB value of 8 to 18 and (C) 1 to 30% by weight of a hydrophobic co-dispersant from the group of fatty alcohols containing 12 to 22 carbon atoms or partial esters of polyols containing 3 to 6 carbon atoms with fatty acids containing 12 to 22 carbon atoms, with the proviso that the ratio of component (B) to component (C) is in the range from 0.5:1 to 20:1, in the presence of 15 to 85% by weight of water to a temperature above the melting point of the mixture of components (A) to (C) and the dispersion obtained is subsequently heated to a temperature within or above the phase inversion temperature range—or the dispersion is directly prepared at that temperature—and is then cooled to a temperature below the phase inversion temperature range and optionally further diluted with water.

Accordingly, the present invention relates to a process for the production of wax dispersions, in which (A) 10 to 80% by weight of a wax are heated with (B) 0.5 to 30% by weight of a hydrophilic nonionic dispersant with an HLB value of 8 to 18 and (C) 1 to 30% by weight of a hydrophobic co-dispersant from the group of fatty alcohols containing 12 to 22 carbon atoms or partial esters of polyols containing 3 to 6 carbon atoms with fatty acids containing 12 to 22 carbon atoms, with the proviso that the ratio of component (B) to component (C) is in the range from 0.5:1 to 20:1, in the presence of 15 to 85% by weight of water to a temperature above the melting point of the mixture of components (A) to (C) and the dispersion obtained is subsequently heated to a temperature within or above the phase inversion temperature range—or the dispersion is directly prepared at that temperature—and is then cooled to a temperature below the phase inversion temperature range and optionally further diluted with water.

The process according to the invention has the advantage that particularly fine-particle dispersions with excellent stability in storage are obtained. In addition, by comparison with the prior art as represented, for example, by DE-OS 38 19 193, the phase inversion temperature is reduced which is particularly favorable in practice by virtue of the resulting saving of energy.

Waxes, i.e. component (A), are understood among experts (cf. for example O.-A. Neumüller, "Römpps Chemie-Lexikon", 7th Edition, Stuttgart 1977, page 3857) to be natural or synthetic substances which are solid and kneadable at 20° C. and coarsely to finely crystalline and which only change into a fluid low-viscosity state without decomposing at temperatures above about 40° C.

There are no limits to the nature and origin of the waxes (A) in accordance with the present invention. Accordingly, the waxes (A) may be selected from each of the three groups in which waxes are normally placed. These three groups are:

1) natural waxes, namely: (a) vegetable waxes which are divided into recent waxes, such as candelilla wax, carnauba wax, Japan wax, esparto grass wax and ouricoury wax, and fossil waxes, such as montan wax, etc.; (b) animal waxes, such as beeswax, shellac wax, spermaceti, lanolin (wool wax), preening wax, etc.; (c) mineral waxes (petroleum waxes), such as ceresine, ozocerite (earth wax), petrolatum, paraffin and microwaxes, 2) chemically modified waxes, for example the oxidized produced from crude montan wax, 3) synthetic waxes, for example from the paraffins obtained by the Fischer-Tropsch process which are converted into a number of hard waxes by oxidation with air, selective solvent treatment, esterification, saponification, etc. Synthetic waxes also include polyethylene waxes which are obtained partly by high-pressure polymerization of ethylene and partly by cracking from high molecular weight low-pressure polyethylene and corresponding oxidized products.

If desired, liquid oils and/or liquid hydrocarbons may be present in addition to the waxes (A). The feature "liquid" applies to the consistency of the oils or hydrocarbons at 20° C.

Suitable oils are, in particular, monoesters and diesters corresponding to general formulae (I), (II) and (III):

$$R^1\text{-COOR}^2 \qquad (I)$$

$$R^2\text{-OOC-}R^3\text{-COOR}^2 \qquad (II)$$

$$R^1\text{-COO-}R^3\text{-OOC-}R^1 \qquad (III)$$

in which $R^1$ is an alkyl group containing 8 to 22 carbon atoms, $R^2$ is an alkyl group containing 3 to 22 carbon atoms and $R^3$ represents alkylene groups containing 2 to 16 carbon atoms, with the proviso that the total number of carbon atoms in compounds (I) to (III) is at least 11.

Oils selected from the monoesters and diesters corresponding to formulae (I), (II) and (III) are known as cosmetic and pharmaceutical oil components and as components of lubricants. Monoesters (I) suitable as oils are, for example, the isopropyl esters of fatty acids containing 12 to 22 carbon atoms, for example isopropyl myristate, isopropyl palmitate, isopropyl stearate, isopropyl oleate. Other suitable monoesters are, for example, n-butyl stearate, n-hexyl laurate, n-dodecyl oleate, isooctyl stearate, isononyl palmitate, isononyl isononanoate, 2-ethylhexyl palmitate, 2-ethylhexyl laurate, isotridecyl palmitate/stearate, 2-hexyldecyl stearate, 2-octyldodecyl palmitate, oleyl oleate, oleyl erucate, erucyl oleate and esters obtainable from technical aliphatic alcohol mixtures and technical aliphatic carboxylic acids, for example esters of saturated and unsaturated fatty alcohols containing 12 to 22 carbon atoms and saturated and unsaturated fatty acids containing 12 to 22 carbon atoms which are obtainable from animal and vegetable fats. Naturally occurring monoester or wax ester mixtures as present, for example, in jojoba oil or in sperm oil are also suitable providing they are liquid at 20° C.

Suitable dicarboxylic acid esters (II) are, for example, di-n-butyl adipate, di-n-butyl sebacate, di-(2-ethylhexyl)-adipate, di-(2-hexyldecyl)-succinate and diisotridecyl azelate. Suitable diol esters (III) are, for example, ethylene glycol dioleate, ethylene glycol diisotridecanoate, propylene glycol di-(2-ethylhexanoate), propylene glycol diisostearate, propylene glycol dipelargonate, butanediol diisostearate and neopentyl glycol dicaprylate.

Other suitable oils are esters of trihydric and polyhydric alcohols, more especially vegetable triglycerides, for example olive oil, almond oil, peanut oil, sunflower oil, or even the esters of pentaerythritol, for example with pelargonic acid or oleic acid.

Suitable fatty acid triglycerides are natural vegetable oils, for example olive oil, sunflower oil, soybean oil, peanut oil, rapeseed oil, almond oil, palm oil and the liquid fractions of coconut oil or palm kernel oil, and animal oils, for example neat's foot oil, the liquid fractions of beef tallow, or even synthetic triglycerides of the type obtained by esterification of glycerol with fatty acids containing 8 to 22 carbon atoms, for example triglycerides of caprylic acid/capric acid mixtures, triglycerides of technical oleic acid or of palmitic/oleic acid mixtures.

Examples of suitable hydrocarbons are, above all, paraffin oils and synthetic hydrocarbons, for example liquid polyolefins, or defined hydrocarbons, for example alkyl cyclohexanes such as 1,3-diisooctyl cyclohexane for example.

Substances suitable as hydrophilic nonionic dispersants (B) are characterized by a lipophilic, preferably linear alkyl or acyl group and by a hydrophilic group formed from low molecular weight glycol, glucose and polyol ethers.

The dispersants (B) are used in the wax dispersions according to the invention in a quantity of 0.5 to 30 parts by weight and preferably in a quantity of 3 to 20 parts by weight.

Suitable dispersants (B) are, in particular, ethylene oxide adducts of fatty alcohols containing 16 to 22 carbon atoms. Corresponding products are commercially available. The technical products are mixtures of homologous polyglycol ethers of the starting fatty alcohols of which the average degree of ethoxylation corresponds to the quantity of ethylene oxide added on in moles. Other suitable dispersants are ethylene oxide adducts with partial esters of a polyol containing 3 to 6 carbon atoms and fatty acids containing 14 to 22 carbon atoms. Products such as these are prepared, for example, by ethoxylation of fatty acid partial glycerides or of mono- and difatty acid esters of sorbitan, for example of sorbitan monostearate or sorbitan sesquioleate. The dispersants suitable for the process according to the invention should have an HLB value of 8 to 18. The HLB value (hydrophilic/lipophilic balance) is understood to be a value which may be calculated in accordance with the following equation:

$$HLB = \frac{100 - L}{5}$$

where L is the percentage by weight of lipophilic groups, i.e. the fatty alkyl or fatty acyl groups in percent, in the ethylene oxide adducts.

Preferred dispersants (B) are fatty alcohol polyglycol ethers (B1) corresponding to general formula (IV):

$$R^4\text{-(O-CH}_2\text{-CH}_2)_n\text{-OH} \qquad (IV)$$

in which $R^4$ is a saturated or unsaturated, linear or branched hydrocarbon radical containing 8 to 22 carbon atoms and preferably 12 to 22 carbon atoms and n is an integer of 10 to 50 and preferably 10 to 30, and adducts of 4 to 20 moles of ethylene oxide with one or more fatty acid partial glycerides (B2).

Fatty acid partial glycerides (B2) of saturated or unsaturated fatty acids containing 10 to 20 carbon atoms are understood to be technical mixtures of fatty acid mono-, di- and triglycerides which are obtained by esterification of 1 mole of glycerol with 1 to 2 moles of a ($C_{10-20}$) fatty acid or by transesterification of 1 mole of a ($C_{10-20}$) fatty acid triglyceride, for example beef tallow, lard, palm oil, sunflower oil or soybean oil, with 0.5 to 2 moles of glycerol. Two types of partial glycerides are commercially available. Partial glycerides of type I contain 35 to 60% of monoglycerides, 35 to 50% of diglycerides and 1 to 20% of triglycerides. Partial glycerides of type II are prepared by molecular distillation from those of type I and contain 90 to 96% of monoglycerides, 1 to 5% of diglycerides and less than 1% of triglycerides (cf.: a) G. Schuster and W. Adams: Zeitschrift für Lebensmitteltechnologie, 1979, Vol. 30(6), pages 256–264; b) G. Schuster (ed.) "Emulgatoren für Lebensmittel" Springer-Verlag, 1985). The fatty acid partial glycerides used in accordance with the invention should contain 35 to 96% of monoglycerides, 1 to 50% of diglycerides and 0.1 to 20% of triglycerides.

Particularly suitable dispersants are adducts of 8 to 12 moles of ethylene oxide with saturated fatty alcohols containing 16 to 22 carbon atoms. Adducts of 8 to 12 moles of ethylene oxide with a saturated fatty alcohol containing 18 to 22 carbon atoms are particularly suitable as dispersants for the emulsification in accordance with the invention of oil components which do not contain any non-polar hydrocarbon oils, i.e. which consist of 50 to 100% by weight of monoesters and diesters corresponding to formulae I, II and III and 0 to 50% by weight of fatty acid triglycerides.

The presence of a co-dispersant (C) in addition to the dispersant (B) is absolutely essential in the process according to the invention. According to the invention, suitable co-dispersants are those of the fatty alcohol type containing 16 to 22 carbon atoms, for example cetyl alcohol, stearyl alcohol, arachidyl alcohol or behenyl alcohol or the mixtures of these alcohols obtained in the industrial-scale hydrogenation of vegetable and animal fatty acids containing 16 to 22 carbon atoms or the corresponding fatty acid methyl esters. Other suitable co-dispersants are partial esters of a polyol containing 3 to 6 carbon atoms and fatty acids containing 14 to 22 carbon atoms. Examples of such partial esters are the monoglycerides of palmitic and/or stearic acid, the sorbitan monoesters and/or diesters of myristic acid, palmitic acid, stearic acid or of mixtures of these fatty acids, the monoesters of trimethylol propane, erythritol or pentaerythritol and saturated fatty acids containing 14 to 22 carbon atoms. Monoesters also include the technical monoesters which are obtained by esterification of 1 mole of polyol with 1 mole of fatty acid and which represent a mixture of monoester, diester and unesterified polyol.

Particularly suitable co-dispersants for the process according to the invention are cetyl alcohol, stearyl alcohol or a glycerol, sorbitan or trimethylol propane monoester of a fatty acid containing 14 to 22 carbon atoms or mixtures of these substances.

The co-dispersants (C) are used in the wax dispersions according to the invention in a quantity of 1 to 30% by weight and preferably in a quantity of 2 to 20% by weight.

As already mentioned, the ratio between components (B) and (C) is a critical parameter to the success of the process according to the invention. The ratio of component (B) to component (C) should be in the range from 0.5:1 to 20:1. A value in the range from 1:1 to 10:1 is preferred. In functional terms, the ratio between components (B) and (C) is adjusted in such a way that the phase inversion temperature of the composition as a whole is above the melting point of the solid wax (A) and below 100° C.

In addition to the components mentioned, other components may be present in the wax dispersion. Interfacial moderators from the group of tocopherols, Guerbet alcohols containing 16 to 20 carbon atoms and steroids containing 1 to 3 OH groups are particularly mentioned in this regard.

Tocopherols are natural substances with the character of vitamin E which are derived from 2-methyl-2-(4',8',12'-trimethyltridecyl)-chroman-6-ol, so-called tocol. They are identified by Greek characters (cf. "Römpps Chemie-Lexikon", O.-A. Neumüller (ed.), 7th Edition, Stuttgart 1977, pages 3615 et seq.). Particular preference is attributed to α-tocopherol, the most commonly occurring and technically the most important tocopherol which, in many cases, is also referred to as the actual vitamin E. Guerbet alcohols are special branched alcohols (cf. for example A. J. O'Lenick Jr., R. E. Bilbo, Soap Cosm. Chem. Spec. 1987 (4) 52). The Guerbet alcohols to be used in accordance with the invention should contain 16 to 20 carbon atoms, for example 2-hexyl decanol or 2-octyl dodecanol. 2-Octyl dodecanol is particularly preferred. Steroids are a group of naturally occurring or synthetic compounds based on the structure of (partly) hydrogenated cyclopenta[a]-phenanthrene, cf. for example O. A. Neumüller, Römpps Chemie-Lexikon, 7th Edition, Stuttgart 1975, pages 3336 et seq. The steroids should contain 1 to 3 OH groups. The sterols in which an OH group is located at the third carbon atom of the steroid skeleton are particularly suitable. The sterols occur in all animal and plant cells. According to their occurrence, they are divided into zoosterols, for example cholesterol, and phytosterols which mainly occur in higher plants. A particularly suitable steroid is cholesterol.

The process according to the invention may be carried out by initially determining the phase inversion temperature by heating a sample of the conventionally prepared dispersion using a conductivity measuring instrument and determining the temperature at which there is a significant reduction in conductivity. The reduction in the specific conductivity of the oil-in-water dispersion initially present from the initial value of around 50 microsiemens per cm to values below about 5 microsiemens per cm normally takes place over a temperature range of 5° to 15° C. The corresponding temperature range is known as the phase inversion temperature range (PIT range).

Once the PIT range is known, the process according to the invention may be carried out either by subsequently heating the dispersion initially prepared in the usual way to a temperature lying within or above the phase inversion temperature range or by carrying out the actual production of the dispersion at a temperature lying within or above the phase inversion temperature range. A water-free or substantially water-free concentrate may also be diluted with hot or cold water at the phase inversion temperature (hot-hot or hot-cold process).

Wax dispersions of the type obtained by the process according to the invention may be used in the cosmetics field, for example as skin-care and body-care formulations. The process according to the invention is particularly suitable for the production of skin and hair treatment formulations. The wax dispersions according to the invention are also suitable for the finishing of textiles, more particularly for sizing (softening).

The following Examples are intended to illustrate the invention without limiting it in any way.

EXAMPLES

1. Substances used
a) Solid waxes (A)
W-1: Paraffin wax ("Paraffin 5213"; ter-HELL)
W-2: Stearyl stearate ("Loxiol G41"; Henkel, Düsseldorf)
b) Dispersants (B)
D-1: Adduct of 10 moles of ethylene oxide with a $C_{22}$ fatty alcohol ("Mergital B10", Sidobre Sinnova)
D-2: Adduct of 40 moles of ethylene oxide with a $C_{16/18}$ fatty alcohol ("Disponil TA40"; Henkel, Düsseldorf)
c) Co-dispersants (C)
CoD-1: Glycerol monostearate ("Cutina GMS" Henkel Düsseldorf)
d) Liquid oils (D)
0-1: Isotridecyl palmitate/stearate ("Loxiol G40"; Henkel, Düsseldorf)
2. Production and characterization of the dispersions
2.1. Production of the dispersions (conventional procedure)
A mixture of components (A) to (C) and water was heated to a temperature just above the melting point of the mixture and homogenized. The composition of the dispersions is shown in Table 1.
2.2. Production of the dispersions according to the invention
The dispersions were prepared as described in 2.1. and then briefly heated (for about 1 minute) to 95° C. The dispersions were then rapidly cooled with stirring to room temperature at a cooling rate of around 2° C. per minute.
2.3. Determination of the phase inversion temperature
Using a conductivity measuring bridge (manufacturer: Radiometer, Copenhagen), the electrical conductivity of the dispersions was determined as a function of temperature. To this end, the dispersion was first cooled to +20° C. At this temperature, the dispersions showed a conductivity of more than 50 microsiemens per cm, i.e. they were present as oil-in-water emulsions. A conductivity graph was drawn up by slow heating at a rate of around 0.5° C./minute which was controlled by a temperature programmer in conjunction with a cryostat. The temperature range in which the conductivity fell to values below 5 microsiemens per cm was recorded as the phase inversion temperature range.

2.4. Evaluation of the emulsions

The phase inversion temperatures (PIT) of the compositions of Examples E1 to E7 and C1 are shown in Table 2.

The viscosity of the compositions according to Table 1 was measured at 25° C./20 r.p.m. using a Brookfield rotational viscosimeter. Spindles 3, 5 or 7 were used according to the viscosity range. The results of the viscosity measurements are shown in Table 2.

Table 2 also indicates the appearance of the dispersion. The blue appearance of the dispersions according to E1 to E7 is indicative of particle sizes below 1 micrometer, i.e. to particular particle fineness of the dispersions.

TABLE 1

Compositions of the dispersions

| | E1 | E2 | E3 | E4 | E5 | E6 | E7 | C1 |
|---|---|---|---|---|---|---|---|---|
| W-1 | 45.0 | 50.0 | 55.0 | 40.5 | 45.0 | 49.5 | 39.0 | 45.0 |
| W-2 | — | — | — | 4.5 | 5.0 | 5.5 | — | — |
| O-1 | — | — | — | — | — | — | 6.0 | — |
| D-1 | 8.2 | 9.1 | 10.0 | 7.1 | 7.9 | 8.7 | 8.2 | — |
| D-2 | — | — | — | — | — | — | — | 10.0 |
| CoD-1 | 1.8 | 2.0 | 2.2 | 2.9 | 3.2 | 3.5 | 1.8 | — |
| Water | 45.0 | 38.9 | 32.8 | 45.0 | 38.9 | 32.8 | 45.0 | 45.0 |

TABLE 2

Characterization of the dispersions

| Dispersion | Viscosity (Pas) | Appearance | PIT Range (°C.) |
|---|---|---|---|
| E1 | 0.7 | Blue dispersion | 80–88 |
| E2 | 11.0 | Blue dispersion | 80–88 |
| E3 | 64.0 | Blue dispersion | 80–88 |
| E4 | 0.5 | Blue dispersion | 80–88 |
| E5 | 4.2 | Blue dispersion | 80–88 |
| E6 | 31.0 | Blue dispersion | 80–88 |
| E7 | 0.7 | Blue dispersion | 75–85 |
| C1 | Solid | 2 Phases | No PIT present |

What is claimed is:

1. The process of producing a storage-stable, fine-particle wax dispersion comprising heating a mixture consisting essentially of
   (A) 10% to 80% by weight of a wax,
   (B) 0.5% to 30% by weight of a hydrophilic nonionic dispersant having an HLB value of 8 to 18, and
   (C) 1% to 30% by weight of a hydrophobic co-dispersant selected from the group consisting of fatty alcohols containing 12 to 22 carbon atoms and partial esters of polyols containing 3 to 6 carbon atoms with fatty acids containing 12 to 22 carbon atoms,
with the proviso that the weight ratio of component (B) to component (C) is in the range from 0.5:1 to 20:1, in the presence of 15% to 85% by weight of water to a temperature above the melting point of the mixture of components (A) to (C) to form a dispersion, heating said dispersion to its phase inversion temperature, and then cooling said dispersion to a temperature below its phase inversion temperature.

2. A process as in claim 1 including adjusting the ratio between components (B) and (C) so that the phase inversion temperature of said dispersion is above the melting point of said wax and below 100° C.

3. A process as in claim 1 wherein said wax is selected from the group consisting of natural waxes, chemically modified waxes, and synthetic waxes.

4. A process as in claim 1 including adding a liquid oil or liquid hydrocarbon to said mixture.

5. A process as in claim 4 wherein said liquid oil is selected from monoesters and diesters corresponding to formulae (I), (II) and (III):

$R^1\text{-COOR}^2$            (I)

$R^2\text{-OOC-R}^3\text{-COOR}^2$            (II)

$R^1\text{-COO-R}^3\text{-OOC-R}^1$            (III)

in which $R^1$ is an alkyl group containing 8 to 22 carbon atoms, $R^2$ is an alkyl group containing 3 to 22 carbon atoms and $R^3$ represents an alkylene group containing 2 to 16 carbon atoms, with the proviso that the total number of carbon atoms in said compounds (I) to (III) is at least 11.

6. A process as in claim 1 wherein said hydrophilic nonionic dispersant contains a lipophilic group and a hydrophilic group.

7. A process as in claim 1 wherein said hydrophilic nonionic dispersant consists essentially of an ethylene oxide adduct of a fatty alcohol containing 16 to 22 carbon atoms.

8. A process as in claim 1 wherein said hydrophobic co-dispersant is selected from the group consisting of cetyl alcohol, stearyl alcohol, glycerol, sorbitan, trimethylol propane monoester of a fatty acid containing 14 to 22 carbon atoms, and mixtures thereof.

9. A process as in claim 1 including adding the product thereof to a cosmetic composition.

10. A process as in claim 9 wherein said cosmetic composition comprises a skin-care or hair-care formulation.

11. A process as in claim 1 including contacting the product thereof with a textile material.

12. A storage-stable, fine-particle wax dispersion consisting essentially of
   (A) 10% to 80% by weight of a wax,
   (B) 0.5% to 30% by weight of a hydrophilic nonionic dispersant having an HLB value of 8 to 18, and
   (C) 1% to 30% by weight of a hydrophobic co-dispersant selected from the group consisting of fatty alcohols containing 12 to 22 carbon atoms and partial esters of polyols containing 3 to 6 carbon atoms with fatty acids containing 12 to 22 carbon atoms,
with the proviso that the weight ratio of component (B) to component (C) is in the range from 0.5:1 to 20:1, and 15% to 85% by weight of water, based on the weight of said dispersion.

13. A wax dispersion as in claim 12 wherein the ratio between components (B) and (C) is adjusted so that the phase inversion temperature of said dispersion is above the melting point of said wax and below 100° C.

14. A wax dispersion as in claim 12 wherein said wax is selected from the group consisting of natural waxes, chemically modified waxes, and synthetic waxes.

15. A wax dispersion as in claim 12 further containing a liquid oil or liquid hydrocarbon.

16. A wax dispersion as in claim 15 wherein said liquid oil is selected from monoesters and diesters corresponding to formulae (I), (II) and (III):

$$R^1\text{-COOR}^2 \quad (I)$$

$$R^2\text{-OOC-}R^3\text{-COOR}^2 \quad (II)$$

$$R^1\text{-COO-}R^3\text{-OOC-}R^1 \quad (III)$$

in which $R^1$ is an alkyl group containing 8 to 22 carbon atoms, $R^2$ is an alkyl group containing 3 to 22 carbon atoms and $R^3$ represents an alkylene group containing 2 to 16 carbon atoms, with the proviso that the total number of carbon atoms in said compounds (I) to (III) is at least 11.

17. A wax dispersion as in claim 12 wherein said hydrophilic nonionic dispersant contains a lipophilic group and a hydrophilic group.

18. A wax dispersion as in claim 12 wherein said hydrophilic nonionic dispersant consists essentially of an ethylene oxide adduct of a fatty alcohol containing 16 to 22 carbon atoms.

19. A wax dispersion as in claim 12 wherein said hydrophobic co-dispersant is selected from the group consisting of cetyl alcohol, stearyl alcohol, glycerol, sorbitan, trimethylol propane monoester of a fatty acid containing 14 to 22 carbon atoms, and mixtures thereof.

* * * * *